US009012490B2

(12) United States Patent
Nwulia et al.

(10) Patent No.: US 9,012,490 B2
(45) Date of Patent: Apr. 21, 2015

(54) LIPOPHILIC CURCUMIN ANALOGS AND METHODS OF INHIBITING HIV-1, TREATING LATENT HIV IN THE BRAIN, AND PREVENTING HIV-MEDIATED COGNITIVE DECLINE AND HIV DEMENTIA

(71) Applicants: Evaristus A. Nwulia, Elkridge, MD (US); Amol Kulkarni, Washington, DC (US)

(72) Inventors: Evaristus A. Nwulia, Elkridge, MD (US); Amol Kulkarni, Washington, DC (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 13/793,755

(22) Filed: Mar. 11, 2013

(65) Prior Publication Data

US 2014/0051742 A1   Feb. 20, 2014

Related U.S. Application Data

(60) Provisional application No. 61/756,892, filed on Jan. 25, 2013, provisional application No. 61/684,316, filed on Aug. 17, 2012.

(51) Int. Cl.

| | |
|---|---|
| *A01N 43/36* | (2006.01) |
| *A61K 31/40* | (2006.01) |
| *A61K 31/12* | (2006.01) |
| *C07C 49/255* | (2006.01) |
| *C07D 207/36* | (2006.01) |
| *C07D 307/60* | (2006.01) |
| *A61K 31/341* | (2006.01) |
| *C07D 333/32* | (2006.01) |
| *A61K 31/381* | (2006.01) |
| *C07C 323/22* | (2006.01) |
| *A61K 45/06* | (2006.01) |
| *A61M 31/00* | (2006.01) |
| *A61K 31/122* | (2006.01) |
| *A61K 31/4025* | (2006.01) |
| *A61K 9/00* | (2006.01) |

(52) U.S. Cl.
CPC .............. *A61K 31/12* (2013.01); *C07C 49/255* (2013.01); *C07D 207/36* (2013.01); *A61K 31/40* (2013.01); *C07D 307/60* (2013.01); *A61K 31/341* (2013.01); *C07D 333/32* (2013.01); *A61K 31/381* (2013.01); *C07C 323/22* (2013.01); *A61K 45/06* (2013.01); *A61M 31/00* (2013.01); *A61K 31/122* (2013.01); *A61K 31/4025* (2013.01); *A61K 9/0043* (2013.01)

(58) Field of Classification Search
None
See application file for complete search history.

(56) References Cited

U.S. PATENT DOCUMENTS

| 7,740,014 B2 | 6/2010 | Djupesland | |
|---|---|---|---|
| 2004/0014721 A1* | 1/2004 | Hensley et al. | 514/64 |
| 2006/0276536 A1* | 12/2006 | Vander Jagt et al. | 514/475 |
| 2012/0053208 A1 | 3/2012 | Li et al. | |
| 2012/0328701 A1 | 12/2012 | Edelson et al. | |

FOREIGN PATENT DOCUMENTS

WO   2008/103346 A1   8/2008

OTHER PUBLICATIONS

Anand et al, Mol. Pharmaceutics, 2007, 4 (6), Nov. 14, 2007.*
Manna et al, Cancer Research, 60, 3838-3847, Jul. 15, 2000.*
Alvarez et al, Journal of Neurochemistry, 2005, 94, 850,861.*
Ataie, Amin, et al., "Curcumin Exerts Neuroprotective Effects Against Homocysteine Intracerebroventricular Injection-Induced Cognitive Impairment and Oxidative Stress in Rat Brain." Journal of Medicinal Food, 2010, vol. 13, No. 4, pp. 821-826.
Barthelemy, S., et al., "Curcumin and curcumin derivatives inhibit Tat-mediated transactivation of type 1 human immunodeficiency virus long terminal repeat." Res. Virol. 1998, vol. 149, pp. 43-52.
Baum, Larry, et al., "Curcumin interaction with copper and iron suggests one possible mechanism of action in Alzheimer's disease animal models." Journal of Alzheimer's Disease, 2004, vol. 6, pp. 367-377.
Chiu, Simon S., et al., "Differential Distribution of Intravenous Curcumin Formulations in the Rat Brain." Anticancer Research, 2011, vol. 31, pp. 907-912.
Cole, Greg M., et al., "Neuroprotective Effects of Curcumin." Adv Exp Med Biol., 2007, vol. 595, pp. 197-212.
Conteas, Chris N., et al., "Treatment of HIV-Associated Diarrhea with Curcumin." Digestive Diseases and Sciences, 2009, vol. 54, pp. 2188-2191.
Cos, Paul, et al., "Plant-Derived Leading Compounds for Chemotherapy of Human Immunodefiency Virus (HIV) Infection—An Update (1998-2007)." Planta Med, 2008, vol. 74, pp. 1323-1337.

(Continued)

*Primary Examiner* — Wu-Cheng Winston Shen
*Assistant Examiner* — Jean Cornet
(74) *Attorney, Agent, or Firm* — Fitch Even Tabin & Flannery LLP

(57) ABSTRACT

Compounds having formulas (I) to (VIII), salts thereof, or combinations thereof and pharmaceutical compositions comprising one or more these compounds are described herein for the treatment of HIV and neurodegenerative effects caused by HIV. Also provided herein are methods and a kit for inhibiting HIV-1, treating latent HIV in the brain, and preventing HIV-mediated cognitive decline and HIV dementia comprising administering the compounds having the formulas (I) to (VIII) and pharmaceutical compositions comprising the compounds having these formulas. The compounds having formulas I through VIII are curcumin analogs which are advantageously characterized as having anti-retroviral, neuroprotective, anti-glucosidase, and anti-HIV integrase properties. In one aspect, the pharmaceutical composition is delivered intranasally.

26 Claims, 3 Drawing Sheets

(56) References Cited

OTHER PUBLICATIONS

Du, Zhi-yun et al., "Alpha-Glucosidase inhibition of natural curcuminoids and curcumin analogs." European Journal of Medicinal Chemistry, vol. 41, 2006, pp. 213-218.
Fuchs, James R., et al., "Structure-activity relationship studies of curcumin analogues." Bioorganic & Medicinal Chemistry Letters, vol. 19, 2009, pp. 2065-2069.
Gomez-Pinilla, Fernando, et al., "Natural mood foods: The actions of polyphenols against psychiatric and cognitive disorders." Nutritional Neuroscience, May 2012, vol. 15, No. 3, pp. 127-133.
Gordon, Odaine N., et al., "Vanillin and ferulic acid: not the major degradation products of curcumin." Cell Press, Trends in Molecular Medicine, Jul. 2012, vol. 18, No. 7, pp. 361-363.
Gupta, S.P., et al., "Design and Development of Integrase Inhibitors as Anti-HIV Agents." Current Medicinal Chemistry, 2003, vol. 10, pp. 1779-1794.
Hurley, Laura L., et al., "Antidepressant-like effects of curcumin in WKY rat model of depression is associated with an increase in hippocampal BDNF." Behavioural Brain Research, 2012, pp. 1-4.
Kulkarni, S.K., et al., "Evaluation of Antidepressant-Like Activity of Novel Water-Soluble Curcumin Formulations and St. John's Wort in Behavioral Paradigms of Despair." Pharmacology, 2012, vol. 89, pp. 83-90.
Kulkarni, S.K., et al., "Potentials of Curcumin as an Antidepressant." The Scienctific World Journal, 2009, vol. 9, pp. 1233-1241.
Kumar, Anil, et al., "Effect of Curcumin on Intracerebroventricular Colchicine-Induced Cognitive Impairment and Oxidative Stress in Rats." Journal of Medicinal Food, vol. 10, No. 3, 2007, pp. 486-494.
Liu JP, et al., "Herbal medicines for treating HIV infection and AIDS (Review)." The Cochrane Library, 2009, Issue 1, 30 pages.
Liu, Yuanbin, et al., "A broadly neuroprotective derivative of curcumin." Journal of Neurochemistry, vol. 105, 2008, pp. 1336-1345.
Masoumi, Ava, et al., "1-alpha,25-dihydroxyvitamin D3 Interacts with Curcuminoids to Stimulate Amyloid-beta Clearance by Macrophages of Alzheimer's Disease Patients." Journal of Alzheimer's Disease, vol. 17, 2009, pp. S1-S4.
Padhye, S., et al., "Perspectives on Chemopreventive and Therapeutic Potential of Curcumin Analogs in Medicinal Chemistry." Mini Rev Med Chem, May 2010, vol. 10, No. 5, pp. 372-387.
Perry, Elaine, et al., "Medicinal Plants and Dementia Therapy: Herbal Hopes for Brain Aging?" CNS Neuroscience & Therapeutics, vol. 17, 2011, pp. 683-698.
Pfeiffer, Erika, et al., "Studies on the Stability of Turmeric Constituents." Journal of Food Engineering, 2003, vol. 56, pp. 257-259.
Sui, Zhihua, et al., "Inhibition of the HIV-1 and HIV-2 Proteases by Curcumin and Curcumin Boron Complexes." Bioorganic & Medicinal Chemistry, vol. 1, No. 6, 1993, pp. 415-422.
"Suicidal Ideation Associated With Duloxetine Use: A Case Series." Journal of Clinical Psychopharmacology, vol. 28, No. 1, Feb. 2008, pp. 101-122.
Taher, Mohiuddin M., et al., "Curcumin inhibits ultraviolet light induced human immunodeficiency virus gene expression." Molecular and Cellular Biochemistry, vol. 254, 2003, pp. 289-297.
Wang, Ying-Jan, et al., "Stability of Curcumin in Buffer Solutions and Characterization of its Degradation Products." Journal of Pharmaceutical and Biomedical Analysis, vol. 15, 1997, pp. 1867-1876.
White, Brett, et al., "Does turmeric relieve inflammatory conditions?" The Journal of Family Practice, vol. 60, No. 3, Mar. 2011, pp. 155-166.
Xu, Ying, et al., "Curcumin reverses impaired hippocampal neurogenesis and increases serotonin receptor 1A mRNA and brain-derived neurotrophic factor expression in chronically stressed rats." Brain Research, vol. 1162, 2007, pp. 9-18.
Yadav, Babasaheb D., "Study of New Curcumin Analogs for the Treatment of ER-alpha Negative Breast Cancers." Doctoral Thesis, The University of Otago, Dunedin, New Zealand, Jan. 4, 2012, 6 pages.
Zhang, Laura, et al., "Curcuminoids enhance amyloid-beta uptake by macrophages of Alzheimer's disease patients." Journal of Alzheimer's Disease, vol. 10, 2006, pp. 1-7.
International Search Report and Written Opinion on Patentablility, International Patent Application PCT/US2014/013158, completed Apr. 11, 2014, 12 pages.

* cited by examiner

LIPOPHILIC CURCUMIN ANALOGS AND METHODS OF INHIBITING HIV-1, TREATING LATENT HIV IN THE BRAIN, AND PREVENTING HIV-MEDIATED COGNITIVE DECLINE AND HIV DEMENTIA

This application claims the benefit of U.S. Provisional Application Ser. No. 61/756,892, filed Jan. 25, 2013, which is incorporated as if fully rewritten herein and U.S. Provisional Application Ser. No. 61/684,316, filed Aug. 17, 2012 which also is incorporated herein as if fully rewritten.

FIELD

This application relates to curcumin analogs and to pharmaceutical compositions containing them. Methods of inhibiting HIV-1, treating latent HIV in the brain, and methods of preventing HIV-mediated cognitive decline and HIV dementia are also provided.

BACKGROUND

Acquired Immune Deficiency Syndrome (AIDS) remains one of the leading causes of morbidity and mortality in the world. In 2011, the United Nations reported that 1.7 million people died from AIDS-related illnesses. According to the United Nations Programme on AIDS, it was estimated that, as of 2011, 34.2 million people worldwide were infected with human immunodeficiency virus (HIV), including 2.5 million people newly infected with HIV in 2011. amfAR, the Foundation for AIDs Research, reported that more than 60 million people have contracted HIV and approximately 30 million people have died of HIV-related causes since the epidemic began.

AIDS deaths reportedly have fallen for five years in a row, down from 2.3 million in 2005 and 2006 to 1.7 million in 2011. With the successful curtailment of the proliferation of HIV in the blood through the introduction of highly-active antiretroviral therapy (HAART), the population of people infected with HIV now live longer, which has led to the emergence of latent HIV brain infections and associated cognitive decline as a major public health threat. However, current HAART treatment does not treat latent HIV brain disease. HIV is known to cross the blood-brain barrier and enter the nervous system early in systemic infection. It has been reported that neurologic disease is the first manifestation of symptomatic HIV infection in many patients, and that the majority of patients with advanced HIV disease have clinically evident neurologic dysfunction. Numerous neurological complications are associated with AIDS, including AIDS dementia complex (ADC), which is also known as HIV-associated dementia (HAD), HIV encephalopathy, and HIV-associated neurocognitive disorder.

Curcumin, a natural product isolated from the rhizome of *Curcuma longa*, has been investigated as a possible HIV treatment. Curcumin has demonstrated a wide range of biological activity, including antioxidant, anti-inflammatory, and anticancer. (Du et al., European J. Medicinal Chemistry, 41:213-218 (2006).) Curcumin also inhibits the enzyme alpha-glucosidase and HIV integrase, which are required by HIV-1 to infect human cells. However, clinical studies of curcumin for HIV treatment have produced unsatisfactory results, which are believed to be due, at least in part, to the rapid metabolism of orally administered curcumin by the liver into metabolites that are inactive and incapable of crossing the blood-brain barrier to become available to the brain (Anand et al. 2007). As such, curcumin does not have the ability to reach the brain in sufficient quantities and duration to protect the brain from HIV-1 toxicity.

In addition, curcumin is poorly absorbable by mouth because it is not very lipophilic (Anand et al. 2007). Animal studies have largely relied on intraperitonial (i.e., injecting inside the abdomen) and intracranial (i.e., injecting into the brain) administrations to achieve biological effects that are seen in in vitro (i.e., direct tissue) treatments. Moreover, previous in vitro studies of curcumin for HIV inhibition have shown that larger concentrations of curcumin (i.e., in micrograms) are needed to exact pharmacological action.

Therefore, a need remains for a composition that is administrable through routes that are feasible for daily human use for HIV treatment and that can reach the brain site for prevention of direct and indirect HIV-mediated toxicity.

SUMMARY

Provided herein are lipophilic curcumin analogs having formulas (I) to (VIII) or pharmaceutical acceptable salts thereof and pharmaceutical compositions comprising one or more of these curcumin analogs having formulas (I) to (VIII) or pharmaceutical acceptable salts thereof. Also provided are methods for treating latent HIV in the brain and preventing HIV-mediated cognitive decline and HIV dementia comprising administering these analogs and/or pharmaceutical compositions comprising one or more lipophilic curcumin analogs having any of formulas (I) to (VIII) or pharmaceutical acceptable salt thereof to a subject adversely affected by HIV in the brain and/or cognitive decline. In another aspect, a method is provided for inhibiting HIV-1 replication, the method comprising inhibiting HIV-1 with one or more curcumin analog having any of formulas (I) to (VIII) or pharmaceutical acceptable salt thereof.

Advantageously, the curcumin analogs described herein also demonstrate enhanced solubility or dispersibility in non-aqueous solvents, such as chlorofluorohydrocarbons, which are commonly used as propellants in intranasal drug delivery systems. Such solubility, dispersibility and lipophilicity mean that the compounds or analogs described herein have the potential to reach the brain more easily to protect it against HIV toxicity. While not wishing to be bound by theory, it is presently believed that the curcumin analogs described herein protect brain cells through stimulating increased levels of neuroprotective factors (e.g., brain-derived neurotrophic factor ("BDNF")) and through increasing survival of neurons.

In a very important aspect, the analogs or pharmaceutical compositions described herein are in suitable form for intranasal delivery. When delivered intranasally, the analog can be absorbed systemically, thereby avoiding massive liver metabolism which affects the natural curcumin compound. In one aspect, the curcumin analog or pharmaceutical composition is dissolved or dispersed and provided in an olfactory neuroplastic device for direct delivery to the brain through the olfactory mucosa in the nose. In yet another very important aspect, the olfactory neuroplastic device is illustrated in the drawings herein. That device may be used to administer the compounds and pharmaceutical compositions which include other agents (such as odorants or other antiviral agents) for the treatment of neurodegenerative diseases. A kit which includes intranasal delivery of one or more compounds of formula I through VIII or pharmaceutical compositions which include one or more of these compounds is also described herein.

In another form, the pharmaceutical compositions and methods described herein may further comprise not only compounds or compositions for the treatment of neurodegenerative diseases but also at least one other antiviral agent effective to inhibit viral replication in a subject for use in combination therapy. Exemplary antiviral agents for use in combination therapy include, for example antiretroviral agents such as nucleoside reverse transcriptase inhibitors, nonnucleoside reverse transcriptase inhibitors, protease inhibitors, integrase inhibitors, fusion inhibitors, and chemokine receptor antagonists.

DETAILED DESCRIPTION

Figure 1:
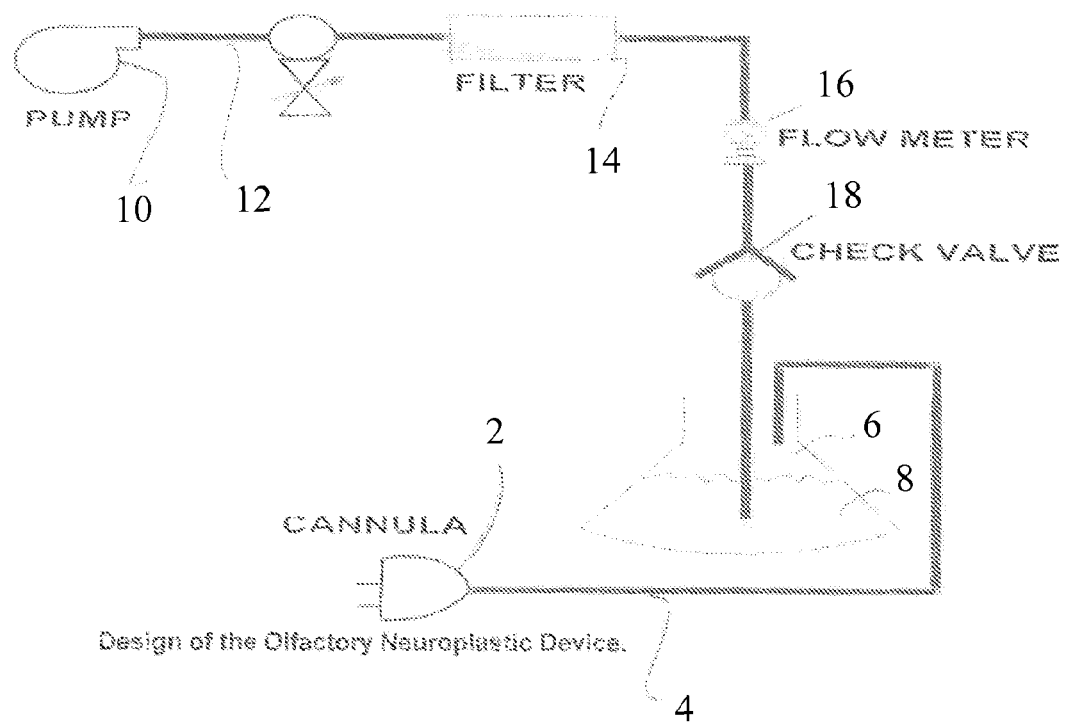
FIG. 1 is an illustration of an exemplary intranasal delivery device suitable for administration of the curcumin analogs described herein.

Provided herein are lipophilic curcumin analogs having the molecular structure of formulas (I) to (VIII) or pharmaceutically acceptable salts thereof and pharmaceutical compositions comprising one or more of these analogs having the structure of formulas (I) to (VIII) or pharmaceutical acceptable salts thereof. These analogs are advantageously characterized by having anti-retroviral, neuroprotective, anti-glucosidase, and anti-HIV integrase properties. These properties make the analogs uniquely suitable as a treatment for neuroAIDS and latent brain HIV disease, as well as for prophylaxis against HIV-mediated cognitive decline and dementia.

Methods for treating latent HIV in the brain and preventing HIV-mediated cognitive decline and HIV dementia are also described herein. These methods comprise administering to a subject in need thereof an effective amount of any of the compounds of formulas (I) to (VIII), pharmaceutically acceptable salts thereof, or combination thereof and/or a pharmaceutical composition comprising one or more of these compounds or salts thereof. In another aspect, a method is provided for inhibiting HIV-1 replication, the method comprising administering one or more compounds of any of formulas (I) to (VIII), pharmaceutically acceptable salts thereof, or combination thereof, including administering a pharmaceutical composition which includes one or more of the compounds and/or pharmaceutically acceptable salts in an amount which is effective for inhibiting HIV-1 replication.

Advantageously, the curcumin analogs (compounds having formulas I through VIII) described herein also demonstrate enhanced solubility or dispersibility in non-aqueous solvents, such as chlorofluorohydrocarbons, which are commonly used as propellants in intranasal drug delivery systems. Such solubility and lipophilicity means that the analogs described herein have the potential to reach the brain more easily to protect it against HIV toxicity. While not wishing to be bound by theory, it is presently believed that the curcumin analogs described herein protect brain cells through stimulating increased levels of neuroprotective factors (e.g., BDNF) and through increasing survival of neurons in the brain.

Because of its enhanced lipophilic properties, the compounds having the formulas provided herein are uniquely suitable for intranasal and sublingual drug delivery. As used herein, "salt" means any pharmaceutically acceptable metal substitute for hydrogen on a phenolic hydrogen or complexed with the formulas described herein. "Pharmaceutically acceptable salt" as used herein means a salt suitable for use in a mammal without undue toxicity or adverse response. The pharmaceutical compositions may also comprise other actives for neurodegenerative diseases as well as conventional excipients, solvents, and/or carriers, if desired.

As used herein, "alkyl" includes straight or branched chain alkyl having 1 to 3 carbons, including for example, methyl, ethyl, n-propyl, isopropyl, and the like. Generally "halogen" includes F, Br, I, or Cl, but preferably is F.

The term "aryl" includes phenyl, optionally substituted at one or more positions with alkyl having 1 to 3 carbons or halogen.

As used herein, lipophilicity refers to the affinity of a compound for a lipophilic environment. By one approach, lipophilicity can be determined using an octanol-water partition coefficient ($K_{ow}$), which represents the ratio of the solubility of a compound in octanol (a non-polar solvent) to its solubility in water (a polar solvent). The higher the $K_{ow}$, the more non-polar the compound. Log $K_{ow}$ values are generally inversely related to aqueous solubility and directly proportional to molecular weight. For purposes herein, lipophilicity values range between 0 to 10 and a value of at least 2.5 indicates good lipophilicity. A log $K_{ow}$ value less than 0 is considered hydrophilic.

One curcumin analog is (1E,4E)-1,5-bis(4-hydroxy-3-methoxyphenyl)penta-1,4-dien-3-one (MW 326.34), which may be formulated and used as described above. This analog was found to be very lipophilic. It has the structure of formula (I):

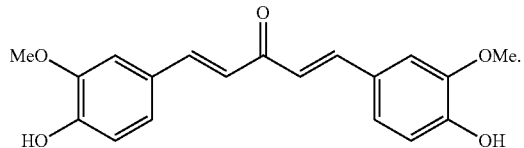

formula (I)

The compound of formula (I) was synthesized by removal of enolizable protons of *curcuma*. This analog has demonstrated superiority over curcumin for inhibition of HIV-1 virus in vitro at nanomolar concentration levels. The removal of enolizable protons was found to augment the lipophilic character of curcumin while enhancing its biological activity (including antiretroviral and neuroprotection). It was found that the compound of formula (I) is able to inhibit HIV at the nanomolar level. This makes the compound a particularly suitable treatment for neuroAIDS and latent HIV brain disease.

A curcumin analog having formula II and pharmaceutical composition which comprises a compound of formula (II) below may be formulated and used as described above:

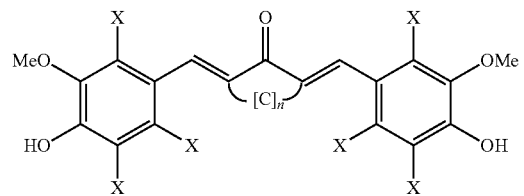 [SMILES: COc1c(O)c(F)c(F)c(/C=C/C(=O)/C=C/c2c(F)c(F)c(O)c(OC)c2F)c1F]

formula (II)

each X is independently selected from H, CH, or halogen (preferably the halogen is F), and n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —CH$_2$ and wherein the carbons of the ring optionally can be substituted with halogen or alkyl having 1 to 3 carbons.

A curcumin analog having formula (III) and pharmaceutical composition which comprises a compound of formula (III) below may be formulated and used as described above:

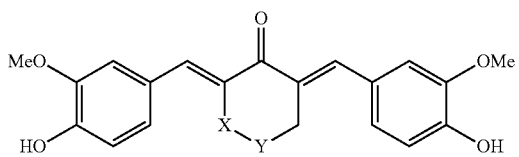

formula (III)

where

X is O, NH, S, or CH$_2$, and

Y is O, NH, S, or CH$_2$.

A curcumin analog having formula IV and pharmaceutical composition which comprises a compound of formula IV below may be formulated and used as described above:

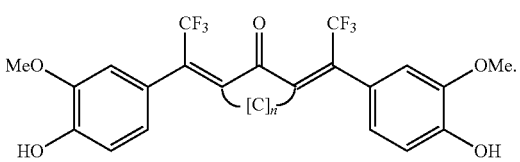

formula (IV)

n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —CH$_2$ and wherein the carbons of the ring optionally can be substituted with halogen or alkyl having 1 to 3 carbons.

A curcumin analog and pharmaceutical composition which comprises a compound of formula (V) below may be formulated and used as described above:

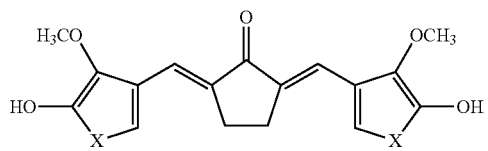

formula (V)

where each X is independently selected from NH, O, or S.

A curcumin analog having formula (VI) and pharmaceutical composition which comprises a compound of formula (VI) below may be formulated and used as described above:

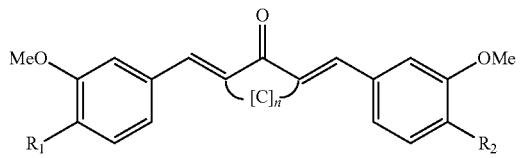

formula (VI)

where $R_1$=alkyl (preferably lower alkyls of 1 to 3 carbons) or phenyl which may be substituted or unsubstituted at any position with halogen or alkyl having 1-3 carbon atoms, $R_2$=halogen, ether, or thioether, and n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —CH$_2$ and wherein the carbons of the ring optionally can be substituted with halogen or alkyl having 1 to 3 carbons.

A curcumin analog having formula (VII) and pharmaceutical composition which comprises a compound of formula (VII) below may be formulated and used as described above:

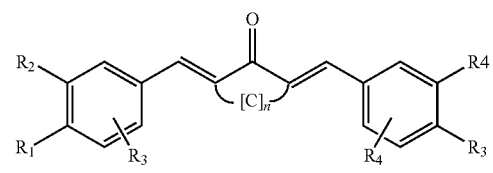

formula (VII)

where $R_1$=phenol, phenolic ether, thiophenol, thioether, halogen, or alkyl;

$R_2$=phenol, phenolic ether, thiophenol, thioether, halogen, or alkyl;

each $R_3$ is independently selected from H, halogen, phenol, and phenolic ether; and $R_4$=H, halogen, phenol, or phenolic ether, n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —CH$_2$ and wherein the carbons of the ring optionally can be substituted with halogen or alkyl having 1 to 3 carbons.

A curcumin analog having formula (VIII) and pharmaceutical composition which comprises a compound of formula (VIII) below may be formulated and used as described above:

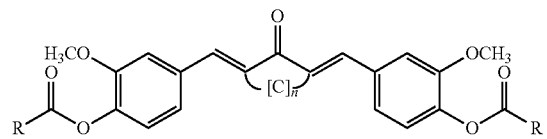

formula (VIII)

where each R is independently selected from alkyl or phenyl, which may optionally be substituted at any position with halogen or alkyl having 1 to 3 carbons, n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —CH$_2$ and wherein the carbons of the ring optionally can be substituted with halogen or alkyl having 1 to 3 carbons.

The pharmaceutical composition includes an effective amount of one or more curcumin analog having formulas (I) to (VIII) or a pharmaceutically acceptable salt of these compounds. By "effective amount" is meant a therapeutically justified or a prophylactically justified amount of the analog. A therapeutically justified amount is the amount of the analog needed to provide a desired biological or medical response in a subject, while a prophylactically justified amount is the amount of the analog needed to prevent, suppress, or slow progress of HIV-mediated cognitive decline and HIV dementia in a subject infected with HIV. In one particular aspect, the subject is a mammal and in another aspect is a human.

The curcumin analogs described herein and pharmaceutical compositions comprising these curcumin analogs can be administered to a subject in need thereof in at a dosage determined upon factors known to one skilled in the art, such as but not limited to timing and route of administration, frequency of treatment, activity of the analog, health of the subject, including weight, age, severity of HIV infection, and the like.

The compounds of formulas (I) to (VIII), pharmaceutically acceptable salts thereof and pharmaceutical compositions which include these compounds are effective for inhibiting HIV-1 replication. A method is provided for inhibiting HIV-1 replication comprising administering these compounds, pharmaceutically acceptable salts thereof, or combinations thereof which may be part of the pharmaceutical composition in effective amounts to inhibit HIV-1 replication.

In another aspect, the compounds of formulas (I) to (VIII), pharmaceutically acceptable salts thereof and pharmaceutical compositions which include these compounds are effective for preventing HIV-mediated cognitive decline and HIV dementia. In this aspect, a method also is provided comprising administering to a subject in need of treatment at least one of these compounds, pharmaceutically acceptable salts, or combinations thereof which may be a part of the pharmaceutical composition in an amount effective to prevent HIV mediated cognitive decline and/or dementia.

In yet another aspect, the compounds of any of formulas (I) to (VIII), pharmaceutically acceptable salt thereof and pharmaceutical compositions comprising one or more of these compounds are effective for treating latent HIV in the brain. In this aspect, a method also is provided comprising administering to a subject in need of treatment of latent HIV in the brain at least one of these compounds of formulas (I) to (VIII), pharmaceutically acceptable salts, or combinations thereof.

As used herein, a subject in need of treatment has tested positive for HIV infection in the past and may have achieved undetectable levels of HIV in the blood (through usual treatment for HIV) but may still have either dormant HIV virus in the brain or HIV-associated immune reactions affecting the brain, with resultant impairment in brain functions (e.g., cognitive decline, mood problems, personality changes or psychosis).

It is also presently believed that the compounds of formulas (I) to (VIII) have anti-hepatitis C activity. A method for treating hepatitis C is also provided, the method comprising administering to a subject in need of treatment at least one of these compounds, pharmaceutically acceptable salts, or combinations thereof which may be a part of the pharmaceutical composition in an amount effective to prevent HIV mediated cognitive decline and/or dementia. A subject in need of hepatitis C treatment has tested positive for hepatitis C infection.

The compounds of formulas (I) to (VIII) or pharmaceutical compositions comprising them as described herein can be applied systemically or locally. The compounds or compositions may be associated with or coated onto nanoparticles for systemic or local administration. The nanoparticles may range in size of from about 10,0000 nanometers to as small as 1 nanometer. The particles may be polymeric, such as polyethylene glycol, albumin, and biocompatible styrene.

In one particularly important aspect, the compounds of formulas (I) to (VIII) and pharmaceutical compositions which include such compounds or pharmaceutically acceptable salts are formulated for intranasal administration. Administration via non-oral routes (e.g., parenteral routes) may avoid hepatic first pass metabolism but result in the analogs being distributed systemically and requiring the analogs have to cross the blood-brain barrier to get into the brain. However, the intranasal administration is one parenteral route that may have less systemic distribution and could reach the brain directly through the olfactory nerve in the nose, avoiding the blood-brain barrier. Such intranasal administration may be through a device which pushes the compositions into the olfactory mucoca of the nose by positive air pressure via a device as described herein. Alternatively such administration may be by nasal spray which carries the active compositions into contact with the olfactory mucoca.

In the aspect where the treatments are intranasally administered, the compounds of formulas (I) to (VIII), pharmaceutically acceptable salts, and pharmaceutical compositions comprising one or more of them can be absorbed systemically, thereby avoiding massive liver metabolism which affects the natural curcumin compound. In one aspect, the curcumin analog is dissolved and provided in an olfactory neuroplastic device for direct delivery to the brain through the olfactory mucosa in the nose.

An exemplary intranasal delivery device is shown in FIG. 1. The apparatus includes cannula 2 having a conduit 4 into a chamber 6 which holds the active ingredient. In one approach, the active ingredient is a curcumin analog provided herein. Pump 10 pumps air at a positive pressure through conduit 12 to filter 14 and flow meter 16 past check valve 18 into chamber 6. The air under positive pressure sweeps the active ingredient from the chamber 6 into conduit 4 and pushes the active ingredient through cannula 2 into the nose of the user. By one approach, the device may be powered by electricity through a 9V adapter plugged to any electrical source, such as a wall outlet. By another approach, the device is portable to permit treatment at locations and times convenient to the subject undergoing treatment. In this aspect, the device is operated with DC current being supplied by a battery and the device has a housing to accommodate the battery. The device may optionally further include an outlet to recharge the battery should rechargeable batteries be used.

In the aspect where the compounds and pharmaceutical compositions are intranasally delivered or administered, the compounds and compositions described are provided in the intranasal delivery device in an amount suitable for a determined treatment regimen, such as for example based on suitable animal models.

In another form, the pharmaceutical compositions and methods described herein may further comprise at least one other antiviral agent effective to inhibit viral replication in a subject for use in combination therapy. Exemplary antiviral agents for use in combination therapy include, for example antiretroviral agents such as nucleoside reverse transcriptase inhibitors, nonnucleoside reverse transcriptase inhibitors, protease inhibitors, integrase inhibitors, fusion inhibitors, and chemokine receptor antagonists. The pharmaceutical compositions and methods described herein may also further comprise at least one other agent for treating neurodegenerative diseases.

In yet another form, a packaged pharmaceutical composition is provided which includes instructions for use of the composition for inhibiting HIV-1, treating latent HIV in the brain, and/or preventing HIV-mediated cognitive decline and HIV dementia.

Advantages and embodiments of the methods and curcumin analogs described herein are further illustrated by the following examples; however, the particular conditions, processing schemes, materials, and amounts thereof recited in these examples, as well as other conditions and details, should not be construed to unduly limit this method. All percentages are by weight unless otherwise indicated.

EXAMPLES

Example 1

Synthesis of Curcumin

Figure 2:
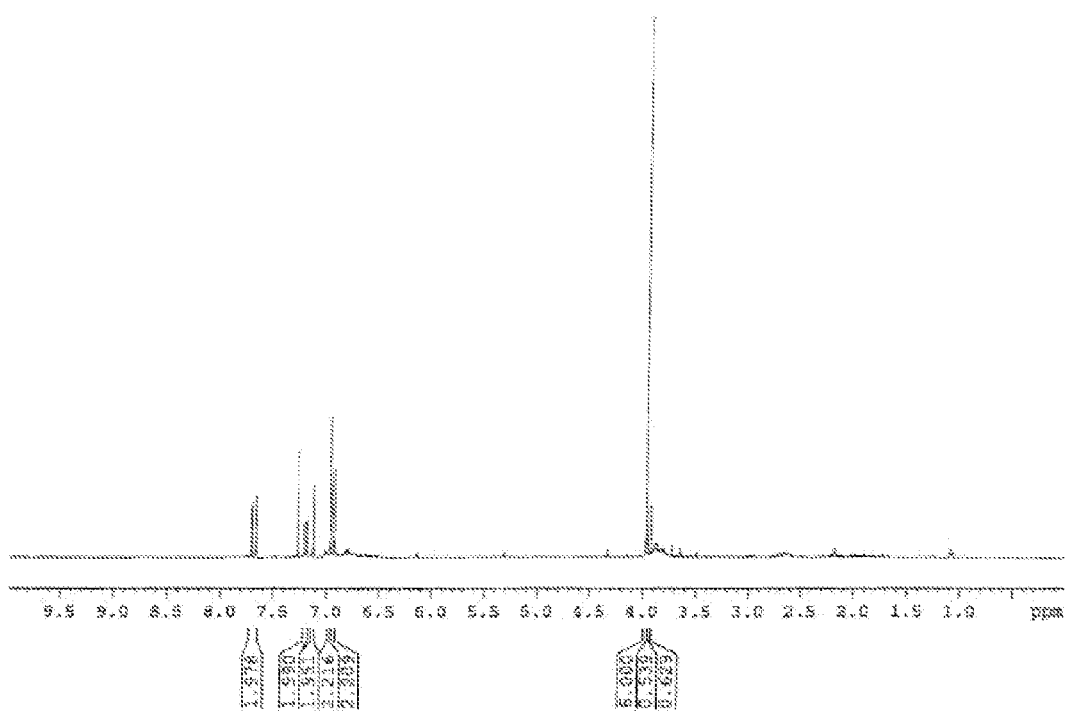
FIG. 2 is a nuclear magnetic resonance spectra (NMR) of the curcumin analog having formula I.

A 50 mL round-bottomed flask was charged with boric oxide (1.75 g, 25.0 mmole) suspended in DMF (5.0 mL). Acetylacetone (2.5 mL, 25.0 mmole) was added, followed by tributyl borate (13.5 mL, 50 mmole). The reaction mixture was warmed to 65° C. and 4-hydroxy-3-methoxybenzaldehyde (vanillin, 7.6 g, 50 mmole) was added followed by the addition of a solution of n-BuNH$_2$ (0.5 mL) and acetic acid (1.5 mL) in acetic acid (5.0 mL). The reaction mixture was heated to 95° C. for 4 hours. It was slowly cooled to 10° C. It was diluted with ethyl acetate (100 mL) followed by the addition of HCl (1N, 250 mL). The reaction mixture was heated to 70° C. and was stirred for 1 hour. The brown solid thus formed was isolated using vacuum filtration. It was thoroughly washed with water and dried. Purification of the crude product using silica gel flash column chromatography (elution with 40% ethyl acetate in hexanes) afforded the desired product (4.1 g, 45% yield) as fluorescent yellow solid. $^1$H- and $^{13}$C-NMR data (FIG. 2) for the synthetic curcumin sample was found to be consistent with previously reported literature.

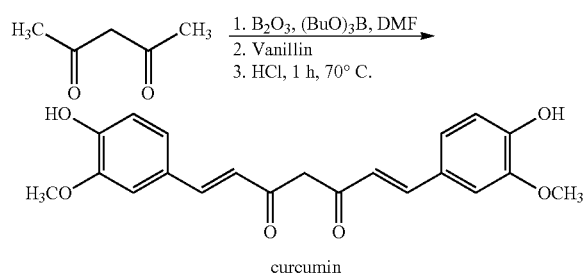

curcumin

Example 2

Synthesis of Curcumin Analog

Glacial acetic acid (10 mL) was saturated with anhydrous hydrogen chloride and was cooled to 0° C. Vanillin (1.52 g, 10 mmole) and acetone (370 µL, 5 mmole) was added and the reaction mixture was stirred at 0° C. for 30 minutes. It was slowly warmed to room temperature and stirred at room temperature for an additional 48 hours. The crude reaction mixture was poured into ice cold water (100 mL). The crude product was washed and dried. The purification by silica gel flash column chromatography (elution with 1% MeOH in CH$_2$Cl$_2$) resulted in the isolation of the curcumin analog. $^1$H- and $^{13}$C-NMR data for the curcumin analog was found to be consistent with previously reported literature.

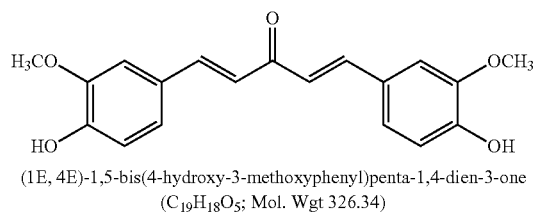

(1E, 4E)-1,5-bis(4-hydroxy-3-methoxyphenyl)penta-1,4-dien-3-one
(C$_{19}$H$_{18}$O$_5$; Mol. Wgt 326.34)

Example 3

Antiretroviral Activity of Curcumin Analogs

Figure 3:
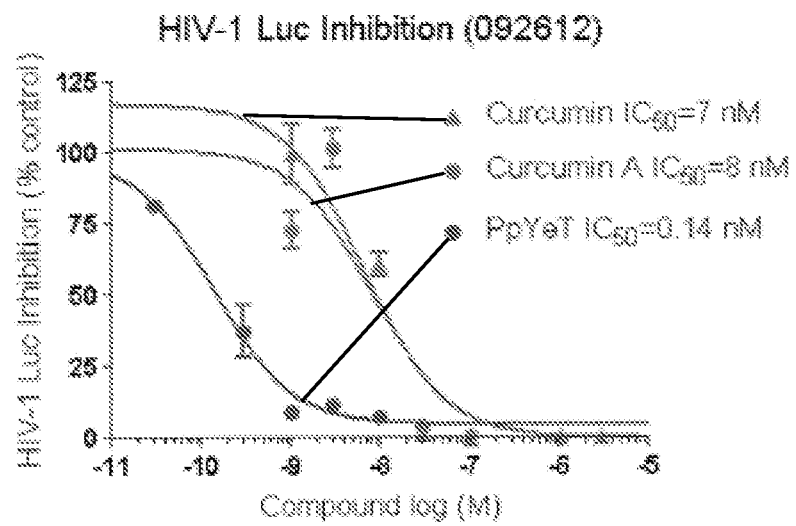
FIG. 3 is a chart showing the anti-HIV action of curcumin analog having formula I compared to curcumin.

The antiretroviral activity of the analog of Example 2 was analyzed in CEM T cells infected with vesicular stomatitus virus glycoprotein (VSVG) pseudotyped HIV-1 pNL 4-3 virus expressing luciferase (VSVG-HIV-1 Luc) and treated with various concentrations of the curcumin analog. The cells were collected at 48 hours post infection, and luciferase activity was analyzed with Luclite Kit (Perkin Elmer) using Labsystems Luminoscan RT equipment (Perkin Elmer). The novel curcumin analog displayed a potent anti-HIV activity with IC50 of 8 nM (FIG. 3). Moreover, the analog also displayed a wider therapeutic index (IC50:cytotoxicity ratio) as compared to curcumin. Enhanced lipophilicity appears to be an important factor in the superior biological activity displayed by the curcumin analog.

Example 4

Curcumin Analogs

Curcumin analogs in accordance with the description herein can be prepared having the structures shown below in Table 1:

TABLE 1

| Structure | Compound | n |
|---|---|---|
| MeO, HO, F — CH=CH—C(=O)—[C]n—CH=CH — OMe, OH, F | Compound 12 | n = 1 |
| | Compound 13 | n = 2 |
| | Compound 14 | n = 3 |
| | Compound 15 | n = 4 |
| MeO, HO / F — ... — F / OMe, OH | Compound 16 | n = 1 |
| | Compound 17 | n = 2 |
| | Compound 18 | n = 3 |
| | Compound 19 | n = 4 |
| MeO, HO, F / F — ... — F / F, OMe, OH | Compound 20 | n = 1 |
| | Compound 21 | n = 2 |
| | Compound 22 | n = 3 |
| | Compound 23 | n = 4 |
| MeO, HO / F, F — ... — F, F / OMe, OH | Compound 24 | n = 1 |
| | Compound 25 | n = 2 |
| | Compound 26 | n = 3 |
| | Compound 27 | n = 4 |
| MeO, HO, F / F, F — ... — F, F / F, OMe, OH | Compound 28 | n = 1 |
| | Compound 29 | n = 2 |
| | Compound 30 | n = 3 |
| | Compound 31 | n = 4 |
| MeO, HO / CF3 — ... — CF3 / OMe, OH | Compound 32 | n = 1 |
| | Compound 33 | n = 2 |
| | Compound 34 | n = 3 |
| | Compound 35 | n = 4 |
| H3CO, HO—X (thiophene/pyrrole/furan) — cyclopentanone — X—OH, OCH3 | Compound 36 | X = NH |
| | Compound 37 | X = O |
| | Compound 38 | X = S |
| MeO, R1 — ... — R2, OMe | Compound 39 | R1 = alkyl; R2 = halogen |
| | Compound 40 | R1 = aryl; R2 = ether |
| | Compound 41 | R1 = alkyl; R2 = thioether | wherein if n = 1 a three membered ring is defined, if n = 2 a four membered ring is defined, if n = 3 a five membered ring is defined, if n = 4 a six membered ring is defined.

Example 4

Effects of Curcumin and a Curcumin Analog on mRNA Levels of BDNF, AKT1, and MAPK1

Along with brain-derived neurotrophic factor ("BDNF"), protein kinase B ("AKT"), and mitogen-activated protein kinase 1 ("MAPK1") (i.e., ERK1/2) genes are known to critically regulate cell survival and growth of neurons during development and the survival and function of adult neurons, as well as modulate synaptic transmission and plasticity. This example compares activities of natural curcumin and curcumin analog (1E,4E)-1,5-bis(4-hydroxy-3-methoxyphenyl) penta-1,4-dien-3-one on AKT, MAPK1 and ERK. The analog was predicted to be more biologically soluble, absorbable, and more resistant to degradation than the natural curcumin. It has already been shown that natural curcumin increases the expression of BDNF in the hippocampus of rats. It was believed that, compared to natural curcumin, the analog would result in greater increase in the activities of these three neuroprotective genes as proof-of-principle of neuroprotection from latent HIV brain disease. The analysis was conducted on CEM cell lines, which are cells that are susceptible to HIV infection.

Figure 4:
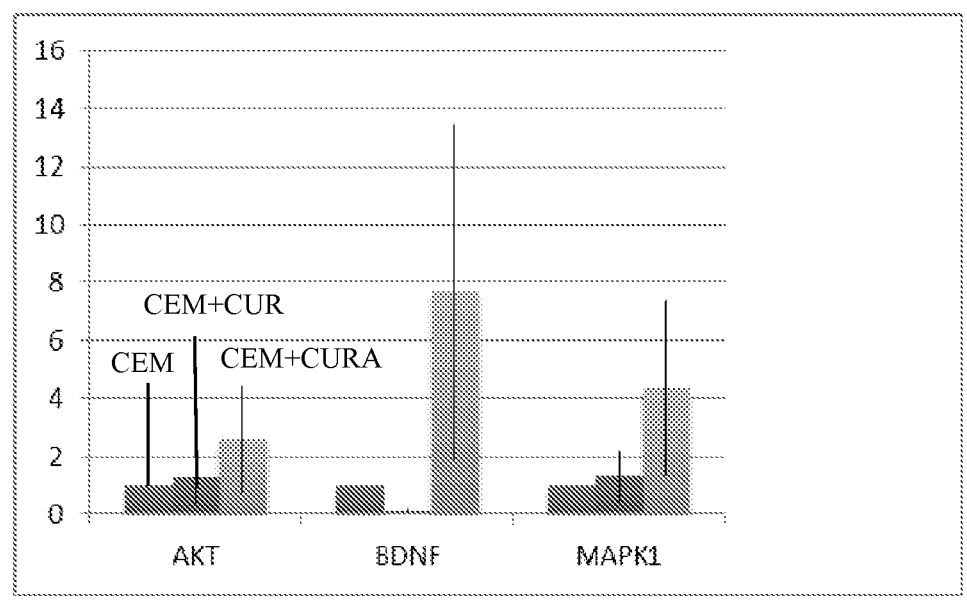
FIG. 4 is a chart showing the effects of curcumin and curcumin analog having formula I on AKT1, BDNF and MAPK1 in CEM cells.

The results are shown in FIG. 4. As shown, curcumin analog significantly increased the mRNA level in AKT1, BDNF and MAPK1. Natural curcumin resulted in a slight increase in AKT and MAPK1 mRNA level but surprisingly resulted in a decrease in the BDNF mRNA level.

It will be understood that various changes in the details, materials, and arrange-ments of the process, formulations, and ingredients thereof, which have been herein described and illustrated in order to explain the nature of the method and resulting curcumin analogs and pharmaceutical compositions, may be made by those skilled in the art within the principle and scope of the embodied method as expressed in the appended claims.

What is claimed is:

1. A method for treating cognitive decline in a subject having HIV, wherein the cognitive decline is mediated by the decrease of BDNF mRNA levels in the brain, the method comprising administering to a subject infected with HIV at least one compound of any of formulas (I) to (VIII), a pharmaceutically acceptable salt thereof, or combination thereof amount in a therapeutically effective amount to increase BDNF mRNA levels in the brain:

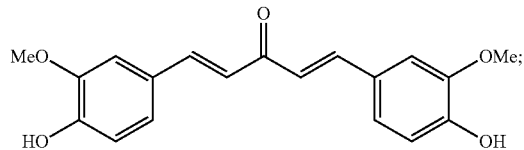

formula (I)

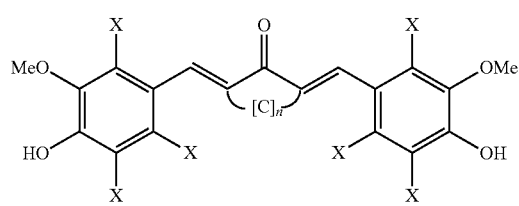

formula (II)

each X is independently selected from H, $CH_3$, or halogen, and n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —$CH_2$ and wherein the carbons of the ring optionally can be substituted with halogen or alkyl having 1 to 3 carbons;

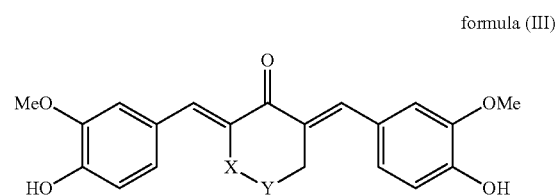

formula (III)

where
X is O, NH, S, or $CH_2$, and
Y is O, NH, S, or $CH_2$;

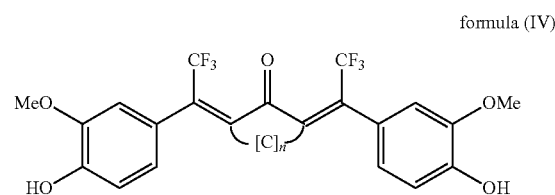 [SMILES: COc1cc(/C(=C/C(=O)/C=C(/c2ccc(O)c(OC)c2)C(F)(F)F)C(F)(F)F)ccc1O]

formula (IV)

n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —$CH_2$ and wherein the carbons of the ring optionally can be substituted with halogen or alkyl having 1 to 3 carbons;

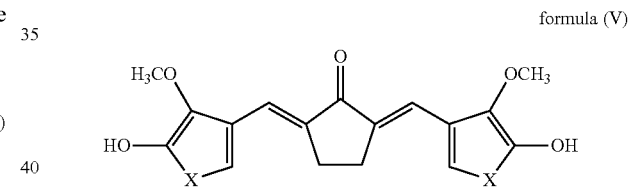

formula (V)

where each X is independently selected from NH, O, or S;

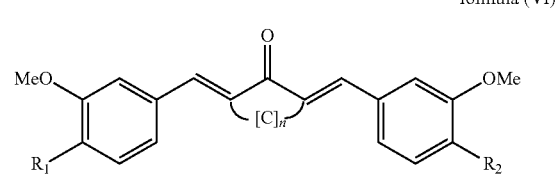

formula (VI)

where
$R_1$=alkyl or phenyl which may be substituted or unsubstituted at any position with halogen or alkyl having 1-3 carbon atoms,
$R_2$=halogen, ether, or thioether, and
n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —$CH_2$ and wherein the carbons of the ring optionally can be substituted with halogen or alkyl having 1 to 3 carbons;

formula (VII)

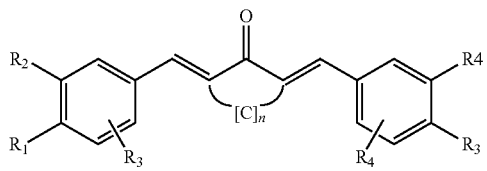

where
R₁=phenol, phenolic ether, thiophenol, thioether, halogen, or alkyl;
R₂=phenol, phenolic ether, thiophenol, thioether, halogen, or alkyl;
each R₃ is independently selected from H, halogen, phenol, and phenolic ether; and
R₄=H, halogen, phenol, or phenolic ether,
n=1 to 5, wherein if n=1 a three membered ring is defined, if n=2 a four membered ring is defined, if n=3 a five membered ring is defined, if n=4 a six membered ring is defined and if n=5 a seven membered ring is defined,
where carbons of the ring may include —CH or —CH₂ and wherein the carbons of the ring optionally can be substituted with halogen or alkyl having 1 to 3 carbons;

formula (VIII)

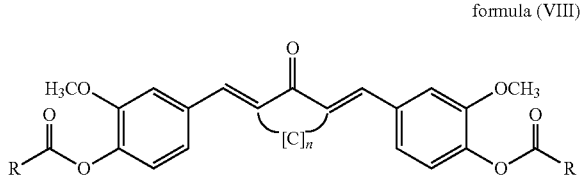

where each R is independently selected from alkyl or phenyl, which may optionally be substituted at any position with halogen or alkyl having 1 to 3 carbons,
n=1 to 5, wherein if n=1 a three membered ring is defined, if n=2 a four membered ring is defined, if n=3 a five membered ring is defined, if n=4 a six membered ring is defined and if n=5 a seven membered ring is defined,
where carbons of the ring may include —CH or —CH₂ and wherein the carbons of the ring optionally can be substituted with halogen or alkyl having 1 to 3 carbons; and
salt thereof, or combination thereof.

2. The method according to claim 1, wherein the at least one compound of any of formulas (I) to (VIII) is intranasally administered.

3. The method according to claim 1, wherein the at least one compound of any of formulas (I) to (VIII) form a part of a pharmaceutical composition which further comprises an antiviral agent other than at least one compound of formulas (I) to (VIII).

4. The method according to claim 3, wherein the antiviral agent is selected from the group consisting of nucleoside reverse transcriptase inhibitors, nonnucleoside reverse transcriptase inhibitors, protease inhibitors, integrase inhibitors, fusion inhibitors, chemokine receptor antagonists, and combinations thereof.

5. The method according to claim 1, wherein the at least one compound of any of formulas (I) to (VIII) is dispersed into a pharmaceutically acceptable oil.

6. The method according to claim 1, wherein the at least one compound of any of formulas (I) to (VIII) form a part of a pharmaceutical composition which is associated with nanoparticles and is intranasally administered.

7. The method according to claim 1, wherein the at least one compound of any of formulas (I) to (VIII) form a part of a pharmaceutical composition which is associated with nanoparticles.

8. The method according to claim 1, wherein R1 is a lower alkyl of 1 to 3 carbons.

9. The method according to claim 1, wherein the at least one compound administered to the subject comprises a compound of formula (I) or a pharmaceutically acceptable salt thereof:

formula (I)

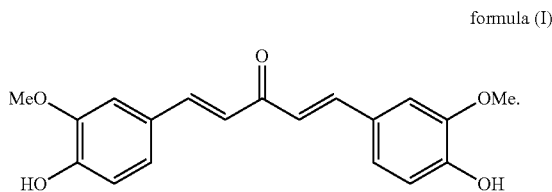 [SMILES: COc1cc(/C=C/C(=O)/C=C/c2ccc(O)c(OC)c2)ccc1O]

10. The method according to claim 9, wherein the compound of formula (I) or a pharmaceutically acceptable salt thereof is dispersed into a pharmaceutically acceptable oil and the administering is by intranasal administration.

11. The method according to claim 1, wherein the at least one compound administered to the subject comprises a compound of formula (II) or a pharmaceutically acceptable salt thereof:

formula (II)

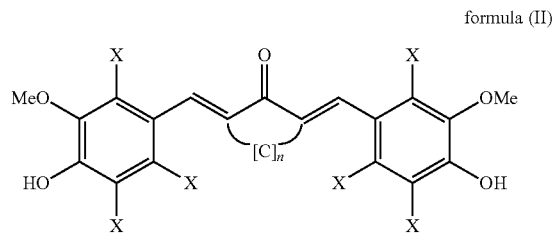

each X is independently selected from H, CH₃, or halogen, and
n=1 to 5, wherein if n=1 a three membered ring is defined, if n=2 a four membered ring is defined, if n=3 a five membered ring is defined, if n=4 a six membered ring is defined and if n=5 a seven membered ring is defined,
where carbons of the ring may include —CH or —CH₂ and wherein the carbons of the ring optionally can be substituted with halogen or alkyl having 1 to 3 carbons.

12. The method according to claim 11, wherein the compound of formula (II) or a pharmaceutically acceptable salt thereof is dispersed into a pharmaceutically acceptable oil and the administering is by intranasal administration.

13. The method according to claim 1, wherein the at least one compound administered to the subject comprises a compound of formula (III) or a pharmaceutically acceptable salt thereof:

formula (III)

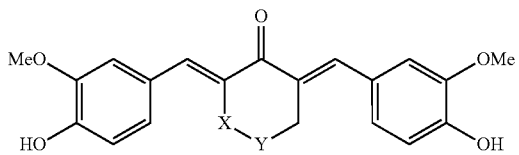

where
X is O, NH, S, or $CH_2$, and
Y is O, NH, S, or $CH_2$.

14. The method according to claim 13, wherein the compound of formula (III) or a pharmaceutically acceptable salt thereof is dispersed into a pharmaceutically acceptable oil and the administering is by intranasal administration.

15. The method according to claim 1, wherein the at least one compound administered to the subject comprises a compound of formula (IV) or a pharmaceutically acceptable salt thereof:

formula (IV)

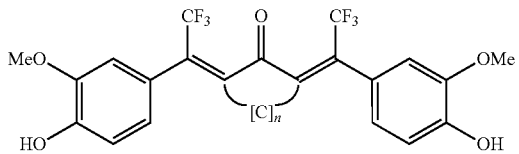

n=1 to 5, wherein if n=1 a three membered ring is defined, if n=2 a four membered ring is defined, if n=3 a five membered ring is defined, if n=4 a six membered ring is defined and if n=5 a seven membered ring is defined,
where carbons of the ring may include —CH or —$CH_2$ and wherein the carbons of the ring optionally can be substituted with halogen or alkyl having 1 to 3 carbons.

16. The method according to claim 15, wherein the compound of formula (IV) or a pharmaceutically acceptable salt thereof is dispersed into a pharmaceutically acceptable oil and the administering is by intranasal administration.

17. The method according to claim 1, wherein the at least one compound administered to the subject comprises a compound of formula (V) or a pharmaceutically acceptable salt thereof:

formula (V)

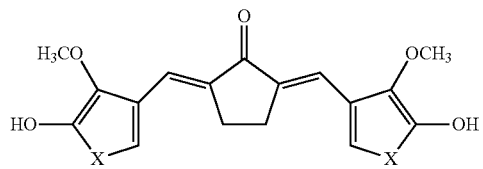

where each X is independently selected from NH, O, or S.

18. The method according to claim 17, wherein the compound of formula (V) or a pharmaceutically acceptable salt thereof is dispersed into a pharmaceutically acceptable oil and the administering is by intranasal administration.

19. The method according to claim 1, wherein the at least one compound administered to the subject comprises a compound of formula (VI) or a pharmaceutically acceptable salt thereof:

formula (VI)

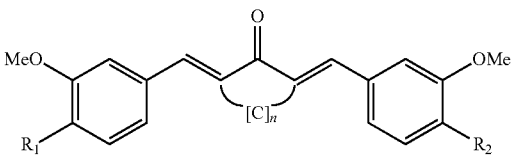

where
$R_1$=alkyl or phenyl which may be substituted or unsubstituted at any position with halogen or alkyl having 1-3 carbon atoms,
$R_2$=halogen, ether, or thioether, and
n=1 to 5, wherein if n=1 a three membered ring is defined, if n=2 a four membered ring is defined, if n=3 a five membered ring is defined, if n=4 a six membered ring is defined and if n=5 a seven membered ring is defined,
where carbons of the ring may include —CH or —$CH_2$ and wherein the carbons of the ring optionally can be substituted with halogen or alkyl having 1 to 3 carbons.

20. The method according to claim 19, wherein R1 is a lower alkyl of 1 to 3 carbons.

21. The method according to claim 19, wherein the compound of formula (VI) or a pharmaceutically acceptable salt thereof is dispersed into a pharmaceutically acceptable oil and the administering is by intranasal administration.

22. The method according to claim 1, wherein the at least one compound administered to the subject comprises a compound of formula (VII) or a pharmaceutically acceptable salt thereof:

formula (VII)

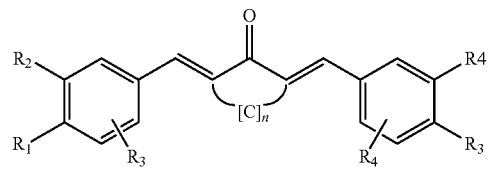

where
$R_1$=phenol, phenolic ether, thiophenol, thioether, halogen, or alkyl;
$R_2$=phenol, phenolic ether, thiophenol, thioether, halogen, or alkyl;
each $R_3$ is independently selected from H, halogen, phenol, and phenolic ether; and
$R_4$=H, halogen, phenol, or phenolic ether,
n=1 to 5, wherein if n=1 a three membered ring is defined, if n=2 a four membered ring is defined, if n=3 a five membered ring is defined, if n=4 a six membered ring is defined and if n=5 a seven membered ring is defined,
where carbons of the ring may include —CH or —$CH_2$ and wherein the carbons of the ring optionally can be substituted with halogen or alkyl having 1 to 3 carbons.

23. The method according to claim 22, wherein R1 is a lower alkyl of 1 to 3 carbons.

24. The method according to claim 22, wherein the compound of formula (VII) or a pharmaceutically acceptable salt thereof is dispersed into a pharmaceutically acceptable oil and the administering is by intranasal administration.

25. The method according to claim 1, wherein the at least one compound administered to the subject comprises a compound of formula (VIII) or a pharmaceutically acceptable salt thereof:

formula (VIII)

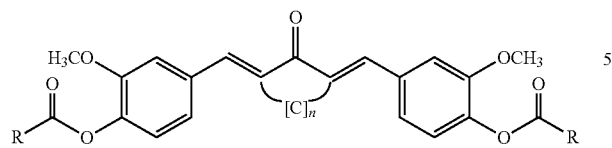

where each R is independently selected from alkyl or phenyl, which may optionally be substituted at any position with halogen or alkyl having 1 to 3 carbons, n=1 to 5, wherein if n=1 a three membered ring is defined, if n=2 a four membered ring is defined, if n=3 a five membered ring is defined, if n=4 a six membered ring is defined and if n=5 a seven membered ring is defined, where carbons of the ring may include —CH or —CH$_2$ and wherein the carbons of the ring optionally can be substituted with halogen or alkyl having 1 to 3 carbons; and salt thereof, or combination thereof.

26. The method according to claim 25, wherein the compound of formula (VIII) or a pharmaceutically acceptable salt thereof is dispersed into a pharmaceutically acceptable oil and the administering is by intranasal administration.

* * * * *